United States Patent [19]

Beaird

[11] Patent Number: 4,658,811
[45] Date of Patent: Apr. 21, 1987

[54] FACIAL CONTOURING MASK

[76] Inventor: Claudette Beaird, P.O. Box 86, Thompsons, Tex. 77481

[21] Appl. No.: 694,702

[22] Filed: Jan. 25, 1985

Related U.S. Application Data

[63] Continuation-in-part of Ser. No. 601,680, Apr. 18, 1984, abandoned.

[51] Int. Cl.⁴ .............................................. A61F 13/12
[52] U.S. Cl. .................................... 128/163; 128/76 B
[58] Field of Search ................ 128/89 A, 163–164, 128/402, 133, 76 R, 76 B, 25 R; 272/94, 95

[56] References Cited

U.S. PATENT DOCUMENTS

| | | |
|---|---|---|
| 84,965 | 12/1868 | Pinckard . |
| 724,812 | 4/1903 | Cloud .............................. 128/163 X |
| 815,426 | 3/1906 | Hardee ............................ 128/164 X |
| 880,718 | 3/1908 | Clendenin ...................... 128/163 X |
| 892,560 | 7/1908 | Smith .............................. 128/163 X |
| 1,023,358 | 4/1912 | Bender ................................ 128/164 |
| 1,216,679 | 2/1917 | Foster ................................. 128/164 |
| 1,274,636 | 8/1918 | Tucker ............................... 128/164 |
| 1,643,090 | 9/1927 | Rogers ............................. 128/76 B |
| 1,855,118 | 4/1932 | Rizer et al. ..................... 128/164 X |
| 1,992,904 | 2/1935 | Preston ........................... 128/89 A |
| 2,024,491 | 12/1935 | Veysey ............................. 128/163 |
| 2,507,617 | 5/1950 | Swendiman ...................... 128/87 |
| 3,572,329 | 3/1971 | DeWoskin ........................ 128/76 |
| 3,709,225 | 1/1973 | Sobel ............................... 128/254 |
| 3,776,244 | 12/1973 | Morgan ...................... 128/76 B X |

FOREIGN PATENT DOCUMENTS 306638 10/1928 United Kingdom ................ 128/164

*Primary Examiner*—John D. Yasko
*Attorney, Agent, or Firm*—Arnold, White & Durkee

[57] ABSTRACT

An adjustable facial contouring mask and method for cosmetic use is disclosed. The facial contouring mask comprises a pad for engagement with the chin and the sides of the face of the wearer. The pad is extremely flexible, having integral elastic bands extending from its ends for securing on the top of the head. The method comprises the steps of fitting the pad under the chin and upwardly along the sides of the face. An anterior band is positioned over the malar bone and a posterior band is positioned adjacent to the ear. Additionally, a strap may be positioned across the front of the face in one of several alternative positions.

4 Claims, 4 Drawing Figures

U.S. Patent    Apr. 21, 1987    4,658,811
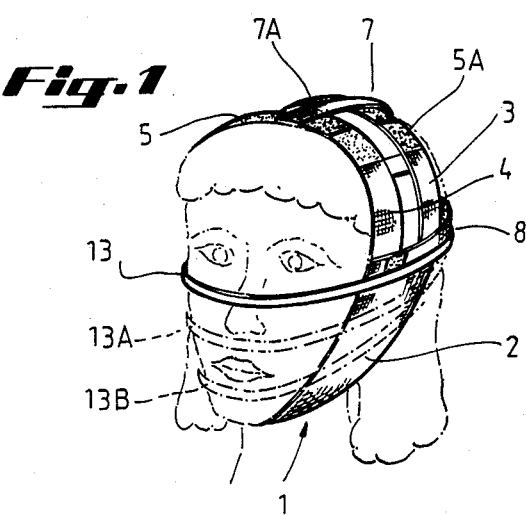
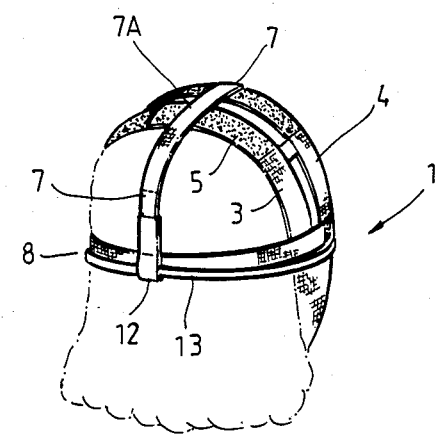
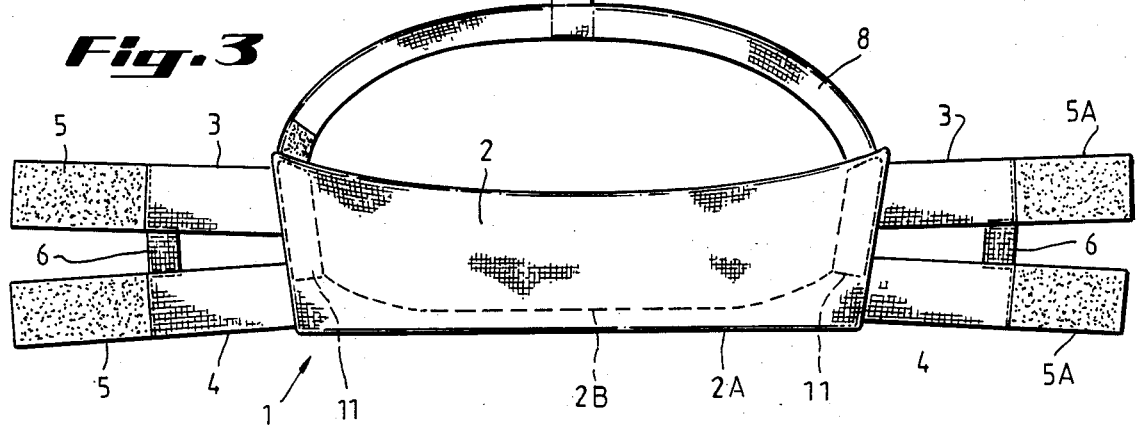
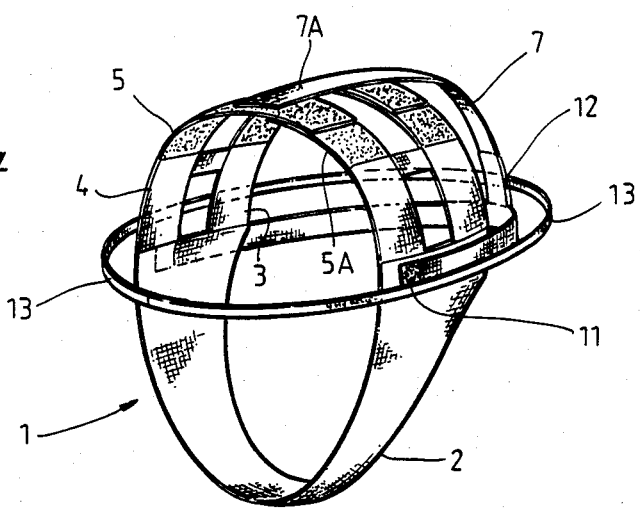

FACIAL CONTOURING MASK

REFERENCE TO RELATED APPLICATION

This application is a continuation-in-part of pending application Ser. No. 601,680, filed Apr. 18, 1984, now abandoned.

BACKGROUND OF THE INVENTION

This invention relates to a novel facial contouring mask capable of being held tightly against the chin and against the sides of the face to postpone such facial aging signs as the jowled look and bags under the eyes.

Contouring masks are utilized to correct a wide number of cosmetic features of the face due to the aging process. Contouring masks are also used to prevent snoring, to correct jaw movements and malocclusions in orthodontics, and for post-operative support after facial surgery.

Some parts of the body cannot comfortably and conveniently be shaped and contoured. For example, the chin and the sides of the face present a problem. Due to the shape of the head and of the face, contouring masks are quite uncomfortable to the wearer even during normal activities such as speaking, eating and exercising. It is of particular interest to provide a contouring mask that is comfortable during aerobic exercises such as running and dancing, since these activities are believed to accelerate facial aging signs.

SUMMARY OF THE INVENTION

The facial contouring mask of the present invention is easy to apply, comfortable to wear and readily adapts itself to the shape of the chin and sides of the face. The mask in its preferred embodiment includes a pad preferably made of an outer stretchable material with a cotton-like cloth lining for support which conforms to the shape of the chin and the sides of the face. The pad is held in place comfortably by two supporting bands which extend upwardly from opposite ends of the pad and are secured by hook and loop type fasteners, such as VELCRO brand, at the top of the head. When the facial contouring mask is worn, one of the supporting bands is located forward to or anterior to the other supporting band. The supporting bands are held closely together by a connecting band that provides additional support for positioning the supporting bands.

BRIEF DESCRIPTION OF THE DRAWINGS

FIG. 1 is a perspective view illustrating a facial contouring mask as it is worn on the head with a strap located in its alternate positions on the crown of the nose, between the nose and the upper lip, and below the lower lip.

FIG. 2 is a perspective view of the facial contouring mask viewed from the rear.

FIG. 3 is a plan view of the facial contouring mask of FIG. 1 as laid out with the straps substantially flat.

FIG. 4 is a perspective view of the facial contouring mask.

DESCRIPTION OF THE PREFERRED EMBODIMENT

Referring to the figures, there is indicated at 1 a facial contouring mask used to withstand the effects of the aging process on cosmetic features of the face to prevent snoring, to correct jaw movements and malocclusions in orthodontics and for post operative support after facial surgery. In general, the mask 1 comprises a pad 2 having an outer stretchable portion 2A and a cotton cloth lining 2B with supporting bands 3 and 4 extending out from its ends. The supporting bands 3 and 4 are secured by the hook and loop type faseners 5 and 5A illustrated in FIGS. 3 and 4.

The pad 2 is preferably contoured along one side to fit the chin and the sides of the face. An arc of an eight inch diameter circle provides a contour to be especially suitable for this purpose. Preferably, the pad 2 should be made of an outer stretchable synthetic or other material 2A with an inner lining of cotton-like material 2B for support. The supporting bands 3 and 4 extend from the ends of the pad 2; they are relatively long and narrow, and are preferably made of an elastic stretchable material. Each part of each supporting band is connected at one end to the pad 2. The other end of each of the supporting bands attach together, preferably at the top of the head. The attaching mechanism is adjustable, such that fitting and tensioning of the supporting bands on the head is facilitated. Hook and loop type fastners 5 and 5A have been found to provide firm but readily adjustable means for interlocking the parts of the supporting bands. As shown in FIG. 3, the fastner consists of a tab 5 with loops and a complimentary tab 5A with hooks such that the tabs 5 and 5A cooperate by means of the hooks and loops to firmly secure the pad 2 to the wearer's chin.

The laterally disposed elastic connecting bands 6 join the elastic supporting bands 3 and 4 to one another, thereby helping to secure the supporting bands 3 and 4 in place when the mask 1 is worn. The harness bands 7 and 8 are designed to help ensure proper positioning of supporting bands 3 and 4. The harness band 7 is worn so that it runs along the head from tabs 5 and 5A on top of the head to a point in the middle of the back of the head where it connects with horizontal harness band 8.

One end of harness band 7 has a hook and loop type fastener portion 7A for securing cooperation with tab 5, and the other end of harness band 7 connects to horizontal harness band 8. These bands can be connected in various ways; however, the use of hook and loop type locking material has been found to be both convenient and effective. Harness bands 7 and 8 may be joined at the back of the head by stitching.

As shown in FIG. 3, the horizontal harness band 8 is connected to and runs horizontally from one end of the pad 2 around the back of the head to connect with the opposite end of the pad 2. Harness band 8 is preferably made of an elastic stretchable material and is secured at each end to the pad 2, preferably by means of hook and loop type fastener material. The fastener strips 11 located on the ends of pad 2 can run the width of the pad 2 between supporting bands 3 and 4 in order to provide adjustment for the head size of the wearer.

As shown in FIG. 1, a strap 13 is horizontally disposed across the face in a position just below the cheek bones and on the crown of the nose. It has been found that this position of strap 13 supports the cheek muscles and thus minimizes sagging tendencies of the cheek muscles by supporting the muscles which affect the contours of the face.

Alternately, strap 13 can be placed in location 13A below the cheek bones and between the upper lip and bottom of the nose as shown in FIG. 1. This position likewise supports the cheek muscles which affect the contour of the face. This alternate position of strap 13

"lifts" the cheek muscles to aid in the support of same and may also aid in correcting malocclusions.

As a second alternative location, strap 13 can be positioned below the lower lip as at 13B in FIG. 1. In this position, the strap also aids in the correction of malocclusions.

Strap 13 extends through a loop 12 formed in strap 7. Loop 12 aids in the horizontal positioning of strap 13. Strap 13 is wrapped around the wearer's face and is attached end-to-end by means of hook and loop type fastners. Strap 13 in the preferred embodiment is made of elastic type material, approximately 27 to 28 inches long with cooperative elements of hook and loop type fastners 9 and 9A each approximately 3 inches long on each end of strap 13. Fastners 9 and 9A permit the wearer of facial contouring mask 1 to adjust strap 13 to its most comfortable tension.

As particularly shown in FIG. 3, the pad 2 is wider than the connecting bands 6. This added width enables the wearer to readily adjust the position of the mask 1. The preferred dimensions of the pad 2 are about thirteen by about five and one-half inches. This pad size has been found to fit comfortably on a variety of persons with firmness and ready adjustability. The mask 1 is designed to have the anterior vertically disposed supporting bands 4 cross the malar bone on each side of the face in the region of the origin of the zygomatic major and the zygomatic minor muscles. The posterior supporting bands 3 is adjacent to each ear, and preferably just forward thereof, depending on the size of the wearer's head. It has been found that the positioning of the anterior vertically disposed supporting bands 4 over the region of the origin of the zygomatic major and the zygomatic minor muscles enables the mask to support these muscles and affect the contours of the face.

To accommodate almost all wearers, it has been found that the connecting bands 6 should be about three inches long and capable of stretching to about 4 inches.

Since the pad 2 allows for contouring to the chin, the facial contouring mask 1 may be comfortably worn for extended periods of time without irritation. Similarly, since the elastic supporting bands 3 and 4 are integral with the pad 2, the usual rivets, metal clips, etc. normally used in contouring masks are eliminated. Hence, a smooth and continuous one-piece assembly is provided for comfort and durability. The tractive force applied to the pad 2 may be readily changed by adjusting the lengths of the elastic supporting bands 3 and 4 with the hook and loop type fastners 5 and 5A. The tractive force is increased by shortening the supporting bands 3 and 4 and is decreased by lengthening the support bands 3 and 4. In a similar manner the tractive forces of strap 13 may be readily changed by adjusting the lengths of the strap with hook and loop type fastners 9 and 9A.

All of the bands are preferably elastic to provide not only an adjustable fit but also tractive forces which result in a firmly snug yet comfortable fit. Elastic stretch fabrics have been found to be especially effective. It is particularly important that supporting bands 3 and 4 and connecting bands 6 be elastic in character.

The use of the facial contouring mask 1 includes fitting the pad 2 under the chin and upwardly along the sides of the head. The elastic supporting bands 3 and 4 hold the pad 2 in place and are secured at the top of the head by the hook and loop type fastners 5 and 5A. The elastic supporting bands 4 is positioned over the malar bone in the region of the origin of the zygomatic major and the zygomatic minor muscles. The elastic supporting bands 3 is positioned adjacent to the ear and preferably just forward thereof. The length of the elastic supporting bands 3 and 4 is adjusted by means of the hook and loop type fastners 5 and 5A. The hook and loop type fastners 5 and 5A allow adjustment of the supporting bands 3 and 4 for fit as well as for the tensile forces desired by the wearer. The elastic connecting bands 6 act to position the elastic supporting bands 3 and 4. The connecting bands 6 are about 3 inches in length and can be made stretchable to about 4 inches, as desired.

If desired, hair clasps (not illustrated) can be attached to supporting bands 3 and 4 and to the wearer's hair to help maintain the position of the contour mask on the wearer. As noted earlier, it is preferred that the several bands in the mask structure be substantially elastic in order to provide both adjustability and a resilient, stretchy quality. The bands can be made of any suitable rubbery stretchable material, but elastic stretch fabrics have been found to be especially effective.

The mask of this invention can be made in several sizes. A mask of wide application, however, is one with the following approximate dimensions. The cotton-like pad 3 can be about 5½ inches by about 13 inches, the connecting bands 6 about 2¼ inches between the supporting bands, and supporting bands 3 and 4 providing a total of about 20 to 22 adjustable inches between the hook and loop type fastners.

As various changes could be made in the above construction without departing from the scope of the invention, it is intended that all matter contained in the above description or shown in the accompanying drawings shall be interpreted as illustrative and not in a limiting sense.

What is claimed is:

1. A facial contouring mask comprising
  a pad consisting essentially of an outer stretchable material and an inner lining of cotton-like cloth adapted to fit under the chin and to extend upwardly along each side of the face, the pad being contoured to fit the neck of the wearer;
  a first pair of elastic anterior supporting bands, adjustable in length, connected at first ends to opposite ends of the anterior portion of the pad to extend upwardly over the malar bone in the region of the origin of the zygomatic major muscles and the zygomatic minor muscles on opposite sides of the face for connection at their second ends;
  a second pair of elastic posterior supporting bands, adjustable in length, connected at first ends to opposite ends of the posterior portion of the pad to extend upwardly adjacent to the ears on opposite sides of the head and substantially parallel to the anterior supporting bands for connection at their second ends;
  adjustable fastening means at second ends of the first pair of anterior supporting bands and at second ends of the second pair of posterior supporting bands;
  a separate elastic connecting band connecting laterally between each pair of adjacent anterior and posterior supporting bands at a point adjacent the adjustable fastening means;
  a first elastic harness band attachable at one end to the first end of one of the second pair of elastic supporting bands and at its other end to the first end of the other one of the second pair of elastic supporting bands; and a second elastic harness band attachable at one end to the second pair of elastic supporting bands and at a second end to an intermediate point along the length of the first harness band.

2. The facial contouring mask as recited in claim 1, wherein the adjustable fastening means are hook and loop type fasteners.

3. The facial contouring mask as recited in claim 1, further comprising an elastic supporting strap horizontally disposed across the front of the face positioned either across the bridge of the nose or under the nose above the upper lip to support the cheek muscles, or below the lower lip to aid in correcting malocclusions.

4. A facial contouring mask comprising
- a pad consisting essentially of an outer stretchable material and an inner lining of cotton-like cloth adapted to fit under the chin and to extend upwardly along each side of the face, the pad being contoured to fit the neck of the wearer;
- a first pair of elastic anterior supporting bands, adjustable in length, connected at first ends to opposite ends of the anterior portion of the pad to extend upwardly over the malar bone in the region of the origin of the zygomatic major muscles and the zygomatic minor muscles on opposite sides of the face for connection at their second ends;
- a second pair of elastic posterior supporting bands, adjustable in length, connected at first ends to opposite ends of the posterior portion of the pad to extend upwardly adjacent to the ears on opposite sides of the head and substantially parallel to the anterior supporting bands for connection at their second ends;
- adjustable fastening means at second ends of the first pair of anterior supporting bands and at second ends of the second pair of posterior supporting bands;
- a separate elastic connecting band connecting laterally between each pair of adjacent anterior and posterior supporting bands at a point adjacent the adjustable fastening means;
- a first elastic harness band attachable at one end to the first end of one of the second pair of elastic supporting bands and at its other end to the first end of the other one of the second pair of elastic supporting bands;
- a second elastic harness band attachable at one end to the second pair of elastic supporting bands and at a second end to an intermediate point along the length of the first harness band; and
- an elastic supporting strap horizontally disposed across the front of the face under the nose above the upper lip to support the cheek muscles.

* * * * *